US006403855B1

(12) United States Patent
Mertens

(10) Patent No.: US 6,403,855 B1
(45) Date of Patent: Jun. 11, 2002

(54) SYNTHESIS OF CRYSTALLINE SILICOALUMINOPHOSPHATES AND USE IN OLEFIN PRODUCTION

(75) Inventor: Machteld M. Mertens, Boortmeerbeek (BE)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/519,975

(22) Filed: Mar. 7, 2000

Related U.S. Application Data

(60) Provisional application No. 60/173,403, filed on Dec. 28, 1999.

(51) Int. Cl.[7] ............ C07C 1/20; B01J 27/182; B01J 29/85; B01J 37/00
(52) U.S. Cl. ............ 585/640; 585/638; 585/639; 502/214; 502/439; 502/514; 423/DIG. 30
(58) Field of Search ............ 585/638, 639, 585/640; 502/439, 514, 214; 423/DIG. 30

(56) References Cited

U.S. PATENT DOCUMENTS

| 4,440,871 | A | * | 4/1984 | Lok et al. ............ 502/214 |
| 4,861,743 | A | | 8/1989 | Flank et al. ............ 502/214 |
| 5,126,308 | A | * | 6/1992 | Barger et al. ............ 502/214 |
| 5,879,655 | A | | 3/1999 | Miller et al. ............ 423/702 |
| 5,958,366 | A | * | 9/1999 | Smith et al. ............ 423/700 |

FOREIGN PATENT DOCUMENTS

EP    0 293 926    12/1988

* cited by examiner

*Primary Examiner*—Walter D. Griffin

(57) ABSTRACT

This invention is directed to a method of making a crystalline silicoaluminophosphate molecular sieve. The method includes adding to a vessel a mixture comprising a silicon containing composition, an aluminum containing composition, a phosphorus containing composition, and a template, and continuously stirring the mixture while applying heat at a temperature and duration effective to form a crystalline silicoaluminophosphate molecular sieve, wherein stirring is applied for 20–95% of the duration that heat is applied. The result is a substantial increase in crystalline molecular sieve product.

18 Claims, No Drawings

SYNTHESIS OF CRYSTALLINE SILICOALUMINOPHOSPHATES AND USE IN OLEFIN PRODUCTION

This application claims priority to U.S. Provisional Patent Application No. 60/173,403, filed Dec. 28, 1999, the entire disclosure of which is incorporated herein by reference.

FIELD OF THE INVENTION

This invention relates to the synthesis of a crystalline silicoaluminophosphate (SAPO) molecular sieve. In particular, this invention relates to increasing the yield of a crystalline SAPO molecular sieve by stirring the starting materials while applying heat at a temperature and duration effective to form a crystalline silicoaluminophosphate molecular sieve, wherein stirring is applied for 20–95% of the duration that heat is applied.

BACKGROUND OF THE INVENTION

Molecular sieves generally have a microporous structure and are composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate. Molecular sieves have a variety of uses. They can be used to dry gases and liquids; for selective molecular separation based on size and polar properties; as ion-exchangers; as catalysts in cracking, hydrocracking, disproportionation, alkylation, isomerization, oxidation, and conversion of oxygenates to hydrocarbons; as chemical carriers; in gas chromatography; and in the petroleum industry to remove normal paraffins from distillates.

Silicoaluminophosphate (SAPO) molecular sieves have become of particular interest recently. These molecular sieves have the ability to convert oxygenates to olefins, aromatics and other compositions. They are especially effective in converting oxygenate compositions such as methanol and dimethyl ether to olefins such as ethylene and propylene.

Various methods of making SAPOs have been disclosed. For example, U.S. Pat. No. 4,440,871 discloses a method of making a SAPO molecular sieve. The method typically involves mixing together a phosphorus containing compound and an aluminum containing compound until a homogeneous mixture is obtained. To the homogeneous mixture is added a template and a silica containing composition, and this mixture is stirred until a final homogeneous mixture is obtained. This final homogeneous mixture is then heated to form a crystalline SAPO molecular sieve.

U.S. Pat. Nos. 4,943,424 and 5,087,347 disclose a method of making a SAPO-11 molecular sieve that is reported to exhibit unique and useful catalytic and shape selective properties. The molecular sieve is made by preparing an aqueous reaction mixture containing aluminum isopropoxide and phosphoric acid. Thereafter, the mixture is combined with silicon oxide. This mixture is then combined with an organic template to form the reaction mixture. The reaction mixture is then pH adjusted and heated to form the crystalline molecular sieve product. Crystallization is conducted in an autoclave and without stirring.

U.S. Pat. No. 5,663,471 discloses a method of making SAPO-34. The method includes mixing together an aluminum containing compound, a phosphorus containing compound, and an acid. This mixture is homogenized and a template material is added. The template added mixture is then homogenized, and the entire mixture is poured into a vessel. The vessel is shaken at room temperature. Then it is heated to form a crystalline molecular sieve product. The product is recovered and dried.

U.S. Pat. No. 5,324,493 discloses a method from crystallizing aluminophosphates and silicoaluminophosphates having an AEL structure using 1,2-bis-(4-pyridyl)-ethane. The method includes mixing together a reactive source of aluminum, phosphorous, and, optionally, silicon, with the addition of 1,2-bis-(4-pyridyl)-ethane. The mixture is heated under autogenous pressure in a closed system to form the crystalline product. The product is isolated after the reaction, washed and dried. Synthesis can be carried out either statically or with stirring.

The known processes for making crystalline silicoaluminophosphate molecular sieves are, unfortunately, very inefficient. In some cases, less than 50 wt % of the reaction components are reacted to form the final crystallized product. The uncrystallized reaction components are typically not recovered and disposed as waste. It is, therefore, desirable to find a reaction process which does not result in a substantial amount of waste.

SUMMARY OF THE INVENTION

In order to overcome the various problems associated with the manufacture of crystalline silicoaluminophosphate molecular sieves, this invention provides a novel method of making crystalline silicoaluminophosphate molecular sieves. The method comprises adding to a vessel a mixture comprising a silicon containing composition, an aluminum containing composition, a template, and a phosphorus containing composition, and stirring the mixture while applying heat at a temperature and duration effective to form a crystalline silicoaluminophosphate molecular sieve, wherein stirring is applied for 20–95% of the duration that heat is applied.

Desirably, heat is applied at a temperature of between 50° C. and 250° C. Heat can also be applied at a duration of between 10 minutes and 240 hours. Desirably, stirring is applied from 20–90% of the duration that heat is applied, more preferably continuous stirring is applied from 30–80% of the duration that heat is applied.

In another embodiment, the silicon containing composition, the aluminum containing composition, the template, and the phosphorus containing composition are added in amounts effective to provide a crystalline molecular sieve composition having a ratio of 0.30–0.34 $SiO_2$/$Al_2O_3$/0.82–0.86 $P_2O_5$. Desirably, the template comprises tetraethyl ammonium hydroxide, more desirably, the template comprises tetraethyl ammonium hydroxide and dipropylamine.

In another embodiment, the invention provides a method of making an olefin product from an oxygenate composition. The method comprises providing a crystalline silicoaluminophosphate molecular sieve made by the method of this invention, calcining the molecular sieve, and contacting the calcined molecular sieve with an oxygenate composition under conditions effective to form an olefin product. Desirably, the oxygenate composition comprises a compound selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. The olefin product is desirably contacted with a polyolefin-forming catalyst under conditions effective to form a polyolefin.

DETAILED DESCRIPTION OF THE INVENTION

Silicoaluminophosphate (SAPO) molecular sieves serve as particularly desirable catalytic materials in converting oxygenate feedstocks to olefin compositions. They are particularly good catalysts for making olefins such as ethylene and propylene from oxygenate compounds.

Silicoaluminophosphate molecular sieves are generally classified as being microporous materials having 8, 10, or 12 membered ring structures. These ring structures can have an average pore size ranging from about 3.5–15 angstroms.

Preferred are the small pore SAPO molecular sieves having an average pore size ranging from about 3.5 to 5 angstroms, more preferably from 4.0 to 5.0 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-18, SAPO-34, SAPO-35, SAPO-44, and SAPO-47, particularly SAPO-18 and SAPO-34, including the metal containing forms thereof, and mixtures thereof As used herein, the term mixture is synonymous with combination and is considered a composition of matter having two or more components in varying proportions, regardless of their physical state.

According to this invention, crystalline SAPO molecular sieves are synthesized by hydrothermal crystallization. In other words, the product of this invention is a crystalline molecular sieve that is formed by reacting the starting materials under hydrothermal conditions to form the crystalline product. In order to significantly increase the conversion of the starting materials to crystalline molecular sieve product, the starting materials are stirred during the crystallization or reaction process. Stirring can be continuous or intermittent, but it is stopped before the reaction process is completed. The reaction process is completed at the effective end of crystallization, at which time it is desirable to discontinue the application of heat.

To make the crystalline silicoaluminophosphate, a reaction mixture is formed by mixing together reactive silicon, aluminum and phosphorus components, along with at least one template. It is ultimately removed by calcining the crystalline product. Calcining the crystalline product means that the template is essentially burned out, leaving behind a porous tunnel like structure within the crystalline product. Once the template is removed, the molecular sieve is described as being activated. That is, it is ready for catalytic use.

Generally, the reaction mixture is sealed and heated, preferably under autogenous pressure to a temperature of at least 50° C. Preferably, the reaction mixture is heated between 50° C and 250° C., more preferably between 100° C. and 225° C.

Heat is applied at a duration effective to form crystalline product. Formation of the final crystalline product can take anywhere from around 30 minutes up to as much as 2 weeks. In some cases, stirring or seeding with crystalline material will facilitate the formation of the product. Preferably heat is applied at a duration of between 10 minutes and 2 weeks, more preferably between 15 minutes and 240 hours, most preferably between 20 minutes and 120 hours.

The mixture is stirred for a time that is less than the duration of the reaction of the components to effectively form the final crystalline molecular sieve product. The duration of the reaction is considered complete at the time that crystallization is effectively completed. This should also correspond to the length of time that the reaction materials are heated. Stirring should be applied from 20–99% of the duration that heat is applied, and most preferably from about 30–85% of the duration that heat is applied. In general, the extent of stirring is affected by crystallization temperature. Typically, the higher the crystallization temperature, the less stirring time is required.

Typically, the crystalline molecular sieve product will be formed in solution. It can be recovered by standard means, however, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system.

The SAPO molecular sieve can contain one or more templates. Templates are generally structure directing agents, and typically contain nitrogen, phosphorus, oxygen, carbon, hydrogen or a combination thereof and can also contain at least one alkyl or aryl group, with 1 to 8 carbons being present in the alkyl or aryl group.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate. The preferred template comprises tetraethyl ammonium hydroxide, preferably, tetraethyl ammonium hydroxide and dipropylamine.

As is known in the art, molecular sieve or catalyst containing the molecular sieve, must be activated prior to use in a catalytic process. Activation is performed in such a manner that template is removed from the molecular sieve, leaving active catalytic sites with the microporous channels of the molecular sieve open for contact with feed. The activation process is typically accomplished by calcining, or essentially heating the template at a temperature of from 200 to 800° C. in the presence of an oxygen-containing gas. In some cases, it may be desirable to heat in an environment having a low oxygen concentration. This type of process can be used for partial or complete removal of the template from the intracrystalline pore system. In other cases, particularly with smaller templates, complete or partial removal from the sieve can be accomplished by conventional desorption processes such as those used in making standard zeolites.

Once the molecular sieve is made, it can be blended with other materials that provide additional hardness or catalytic activity to the finished catalyst product. When blended, the resulting composition is typically referred to as a silicoaluminophosphate (SAPO) catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve which is contained in the final catalyst product ranges from 10 to 90 weight percent of the total catalyst, preferably 30 to 70 weight percent of the total catalyst.

The molecular sieve synthesized in accordance with the present method can be used to dry gases and liquids; for selective molecular separation based on size and polar properties; as an ion-exchanger; as a catalyst in cracking, hydrocracking, disproportionation, alkylation, isomerization, oxidation, and conversion of oxygenates to hydrocarbons; as a chemical carrier; in gas chromatography; and in the petroleum industry to remove normal paraffins from distillates. It is particularly suited for use as a catalyst in cracking, hydrocracking, disproportionation, alkylation, isomerization, oxidation, and conversion of oxygenates to hydrocarbons. Most particularly, the molecular sieve is suited for use as a catalyst in the conversion of oxygenates to hydrocarbons.

In its most preferred embodiment, the SAPO molecular sieve is used as a catalyst in the conversion of oxygenates to hydrocarbons. In this process a feed containing an oxygenate contacts crystalline molecular sieve in a reaction zone of a reactor at conditions effective to produce light olefins, particularly ethylene and propylene. Typically, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 500° C. is preferred.

The process can be carried out in a dynamic bed system or any system using a variety of transport beds, although a fixed bed system could be used. It is particularly desirable to operate the reaction process at high space velocities.

The conversion of oxygenates to produce olefins is preferably carried out in a large scale continuous catalytic reactor. This type of reactor includes fluid bed reactors and concurrent riser reactors as described in "Free Fall Reactor," *Fluidization Engineering*, D. Kunii and O. Levenspiel, Robert E. Krieger Publishing Co. N.Y., 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems*, pages 48–59, F. A. Zenz and D. F. Othmo, Reinhold Publishing Corp., N.Y. 1960, the descriptions of which are expressly incorporated herein by reference.

Any standard commercial scale reactor system can be used, however, including fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

It is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock.

One or more inert diluents may be present in the feedstock, for example, in an amount of from 1 to 95 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof Preferred oxygenate compounds are methanol, dimethyl ether, or a mixture thereof The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered from this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

Comparative Examples A

A1. Unseeded Static Synthesis

An alumina slurry was prepared by mixing together 68.06 parts of Alumina Pural SB of Condea and 110.15 parts of distilled water. To this mixture was added a solution containing 115.74 parts of phosphoric acid (85 wt. % ACROS), using 24.9 parts rinse water, and mixed until homogeneous. Then 22.50 parts of Ludox AS40 (40 wt. % of $SiO_2$) were added using 10.20 parts of rinse water, and the mixture was stirred until homogeneous. To the homogeneous mixture was added 183.31 parts of a 40 wt. % solution of tetraethyl ammonium hydroxide (TEAOH, Eastern Chemical), using 43.17 parts of rinse water. The gel was mixed until homogeneous and 80.79 parts of dipropylamine (DPA) were added using 26.27 parts of rinse water. When the mixture was visually homogeneous, 237.3 parts were transferred to a stainless steel autoclave, heated in 2 hours to 175° C., and kept at this temperature for 60 hours.

A2. Seeded Static Synthesis

To 433.7 parts of the mixture made in A1 were added 2.78 parts of a slurry containing 6.4 wt. % of chabasite crystals. The mixture was stirred until homogeneous. Then, 181.5 parts of the gel were transferred to a stainless steel autoclave, heated in 2 hours to 175° C., and kept at this temperature for 60 hours.

A3. Seeded "Tumbled" Synthesis 98.9 parts of the homogeneous mixture obtained in A1 were transferred to another stainless steel autoclave. This autoclave was mounted on the axis inside an oven and tumbled at 60 rpm, heated in 2 hours to 175° C., and kept at this temperature for 60 hours, with stirring continuing throughout the heating process.

The molar compositions of the synthesis mixtures described in A1–A3 were as follows:

0.3$SiO_2$/$Al_2O_3$/$P_2O_5$/TEAOH/ 1.6DPA / 52$H_2O$.

After the indicated crystallization time, the solids were quantitatively recovered from the mother liquid by centrifuging. The washed solids were dried at 120° C., and an XRD pattern was recorded.

The results of A1–A3 are summarized in the Table 1.

TABLE 1

| Example | Seeds | Temp (C.) | Time (hrs) | Agitation | Yield (wt. %)* |
|---|---|---|---|---|---|
| A1 | – | 175 | 60 | – | 11.1 |
| A2 | + | 175 | 60 | – | 10.7 |
| A3 | + | 175 | 60 | + | 7.8 |

*Yield is expressed as dried product recovered per 100 g of synthesis mixture heated These results indicate that stirring throughout the heating process reduces the yield of recovered product, even for seeded synthesis mixtures.

Comparative Examples B

B1. Seeded Stirred Synthesis

A seeded mixture having approximately the same molar composition as in A1 was prepared similar to A2. The mixture was heated in 8 hours to 175° C. in a 2 liter stainless steel Parr autoclave. The mixture was then stirred at 144 rpm using a combination of the Parr anchor and propeller mixing blades. Mixing was continued during the whole hydrothermal treatment of 60 hours at 175° C. The solids was recovered from the mother liquor by centrifuging, washed and dried. The yield of dried product was 7.5 wt. % of pure SAPO-34.

B2. Seeded Static Synthesis

A seeded mixture was prepared as in B1. The mixture was heated static (without stirring) for 60 hours at 175° C. From this synthesis 12.5 wt. % of pure SAPO-34 was recovered.

EXAMPLES 1 and 2

Two mixtures having approximately the same molar composition as in Comparative Examples A1 and B2 were prepared. The mixtures were heated in an autoclave having the same volume, same mixing blades, etc., as in Example B2.

EXAMPLE 1

The first mixture was heated in 8 hours to 165° C. and maintained for 5 hours at 165° C. under continuous stirring at 80 rpm. Stirring was then stopped, but heating was continued for an additional 19 hours. After crystallization (i.e., at the end of the heating process) 13.4 wt. % of pure SAPO-34 was recovered.

EXAMPLE 2

The second mixture was heated in 8 hours to 175° C. and maintained for 5 hours at 175° C. under continuous stirring. Stirring was then stopped, but heating was continued for an additional 5 hours. After crystallization 12.3 wt. % of pure SAPO-34 was recovered.

Examples 1 and 2 illustrate the advantage of semi-static synthesis (i.e., stirring for less than the entire duration of heating) for SAPO-34.

EXAMPLE 3

A mixture having approximately the same molar composition as in Comparative Example A1 was prepared. The mixture was heated to 170° C. in 12 hours in a commercial scale unit with continuous stirring. The unit was maintained at 170° C. for 54 hours with continuous stirring, then stirring was stopped. The yield at this point was approximately 11 wt. % crystalline molecular sieve. After stirring was stopped, the unit was maintained at 170° C. for an additional 10 hours, at which time crystallization effectively ceased. At this point, the yield was approximately 13 wt. %.

EXAMPLE 4

A mixture having approximately the same molar composition as in Comparative Example A1 was prepared. The mixture was heated to 170° C. in 11 hours in a commercial unit with continuous stirring. The unit was maintained at 170° C. for 30 hours with continuous stirring, then stirring was stopped. The yield at this point was approximately 11.8 wt. % crystalline molecular sieve. After stirring was stopped, the unit was maintained at 170° C. for an additional 10 hours, at which time crystallization effectively ceased. At this point, the yield was approximately 13 wt. %.

Having now fully described this invention, it will be appreciated by those skilled in the art that the invention can be performed within a wide range of parameters within what is claimed, without departing from the spirit and scope of the invention.

What is claimed is:

1. A method of making a crystalline silicoaluminophosphate molecular sieve comprising adding to a vessel a mixture comprising a silicon containing composition, an aluminum containing composition, a template, and a phosphorous containing composition, and stirring the mixture while applying heat at a temperature and duration effective to form a crystalline silicoaluminophosphate molecular sieve, wherein stirring is applied for 20–95% of the duration that the heat is applied, including during the crystallization process.

2. The method of claim 1, wherein the heat is applied at a temperature of between 50° C. and 250° C.

3. The method of claim 1, wherein the heat is applied at a duration of between 10 minutes and 240 hours.

4. The method of claim 1, wherein stirring is applied from 20–90% of the duration that the heat is applied.

5. The method of claim 1, wherein stirring is applied from 30–85% of the duration that the heat is applied.

6. The method of claim 1, wherein the silicon containing composition, the aluminum containing composition, the template, and the phosphorus containing composition are added in amounts effective to provide a molecular sieve composition having a molar ratio of 0.30–0.34 $SiO_2/Al_2O_3/$ 0.82–0.86 $P_2O_5$.

7. The method of claim 1, wherein the template comprises tetraethyl ammonium hydroxide.

8. The method of claim 1, wherein the template comprises tetraethyl ammonium hydroxide and dipropylamine.

9. A method of making an olefin product from an oxygenate composition, comprising providing a crystalline silicoaluminophosphate molecular sieve made by adding to a vessel a mixture comprising a silicon containing composition, an aluminum containing composition, a template, and a phosphorous containing composition, and stirring the mixture while applying heat at a temperature and duration effective to form a crystalline silicoaluminophosphate molecular sieve, wherein stirring is applied for 20–95% of the duration that the heat is applied, including during the crystallization process;

heating the molecular sieve to form a calcined molecular sieve; and contacting the calcined molecular sieve with an oxygenate composition under conditions effective to form an olefin product.

10. The method of claim 9, wherein the heat is applied at a temperature of between 50° C. and 250° C.

11. The method of claim 9, wherein the heat is applied at a duration of between 10 minutes and 240 hours.

12. The method of claim 9, wherein stirring is applied from 20–90% of the duration that the heat is applied.

13. The method of claim 9, wherein stirring is applied from 30–85% of the duration that the heat is applied.

14. The method of claim 9, wherein the silicon containing composition, the aluminum containing composition, the template, and the phosphorus containing composition are added in amounts effective to provide a molecular sieve composition having a molar ratio of 0.30–0.34 $SiO_2/Al_2O_3/$ 0.82–0.86 $P_2O_5$.

15. The method of claim 9, wherein the template comprises tetraethyl ammonium hydroxide.

16. The method of claim 9, wherein the template comprises tetraethyl ammonium hydroxide and dipropylamine.

17. The method of claim 9, wherein the oxygenate composition comprises a compound selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

18. The method of claim 9, wherein the olefin product is contacted with a polyolefin-forming catalyst under conditions effective to form a polyolefin.

* * * * *